United States Patent
Cordeiro et al.

(10) Patent No.: US 9,539,203 B2
(45) Date of Patent: Jan. 10, 2017

(54) PHARMACEUTICAL COMPOSITION COMPRISING A VITAMIN E DERIVATIVE AND A CELL DEATH MARKER

(75) Inventors: Francesca Cordeiro, London (GB); Stephen Moss, London (GB)

(73) Assignee: UCL BUSINESS PLC, London (GB)

( * ) Notice: Subject to any disclaimer, the term of this patent is extended or adjusted under 35 U.S.C. 154(b) by 199 days.

(21) Appl. No.: 12/809,262

(22) PCT Filed: Dec. 19, 2008

(86) PCT No.: PCT/GB2008/004233
§ 371 (c)(1),
(2), (4) Date: Jul. 21, 2010

(87) PCT Pub. No.: WO2009/077769
PCT Pub. Date: Jun. 25, 2009

(65) Prior Publication Data
US 2010/0278747 A1    Nov. 4, 2010

(30) Foreign Application Priority Data
Dec. 19, 2007    (GB) .................................. 0724772.9

(51) Int. Cl.
| | | |
|---|---|---|
| *A61K 51/00* | (2006.01) |
| *A61M 36/14* | (2006.01) |
| *A61K 9/00* | (2006.01) |
| *A61K 47/22* | (2006.01) |

(52) U.S. Cl.
CPC ............. *A61K 9/0048* (2013.01); *A61K 47/22* (2013.01)

(58) Field of Classification Search
CPC ........ A61K 51/00; A61K 51/02; A61K 51/06; A61K 51/08; A61K 51/087; A61K 2123/00; A61K 2121/00; A61K 38/00; A61K 51/086; A61K 51/088; A61K 9/0048; A61K 47/22

USPC   424/1.11, 1.65, 1.69, 1.73, 1.49, 9.1; 514/1, 1.1

See application file for complete search history.

(56) References Cited

U.S. PATENT DOCUMENTS

| | | | | |
|---|---|---|---|---|
| 5,198,432 A | * | 3/1993 | Fariss ........................... | 514/182 |
| 5,886,030 A | * | 3/1999 | Maniar ......................... | 514/458 |
| 2011/0014270 A1 | * | 1/2011 | Holers et al. ................ | 424/450 |

FOREIGN PATENT DOCUMENTS

| | | | |
|---|---|---|---|
| EP | 1464341 | * | 3/2004 |
| EP | 1464341 A | | 10/2004 |
| WO | 03090682 A | | 11/2003 |

OTHER PUBLICATIONS

Serbecic et al (Japanese Journal of Ophthalmology, 2005, vol. 49, No. 5, pp. 355-362).*
Van Heerde et al (Cardiovascular Research, 2000, vol. 45, pp. 549-559).*
Takahashi et al (Biochemical Pharmacology, 2004, vol. 67, No. 2, pp. 315-324).*
ISA/EPO, International Search Report and Written Opinion for International Application No. PCT/GB2008/004233, completed Dec. 16, 2009.
Rowelski et al., "Evaluation of Antioxidant Activity of Alpha-Tocopherol and Quercetin During Oxidation of Phosphatidylcholine Using Chemiluminescent Detection of Lipid Hydroperoxid3S," Pol. J. Food Nutr. Sci., 2009, vol. 59, No. 2, pp. 123-127.

* cited by examiner

*Primary Examiner* — D L Jones
(74) *Attorney, Agent, or Firm* — Stites & Harbison, PLLC; Mandy Wilson Decker

(57) ABSTRACT

The invention relates to a carrier for delivering agents to the posterior region of the eye, the carrier comprising a Vitamin E derivative, especially tocopherol. The carrier may also comprise a cell death marker, such as an annexin.

15 Claims, 13 Drawing Sheets

α- tocopherol

δ- tocopherol

γ- tocopherol

α-tocopherol with (left) and without (right) Anx-F.

α-tocopherol with fluorescein sodium with annexin 5 (left) and without annexin 5 (right)

Notice high level of fluorescence on annexin 5 (left) eye.

δ- tocopherol with (left) and without Anx-F (right)

γ- tocopherol with (left) and without Anx-F (right)

Fluorescein Sodium : Images taken at baseline (left) and 2hrs after administration with combination of annexin & vitamine E derivative.

YoPro: Images taken at baseline (left) and 2hrs after administration with combination of annexin & vitamine E derivative.

PHARMACEUTICAL COMPOSITION COMPRISING A VITAMIN E DERIVATIVE AND A CELL DEATH MARKER

The invention relates to the use of Vitamin E derivatives such as tocopherol, its derivatives and related molecules, as a carrier for the delivery of pharmaceutical or other agents to the retina, particularly when delivered topically.

The delivery of molecules to the posterior region of the eye from topical dosing has been a goal set by many ocular pharmacologists. It has become increasingly popular with the advent of anti-VEGF therapies for age-related macular degeneration and diabetic retinopathy.

Typically topical ocular drug administration is accomplished by eye drops, but they have only a short contact time on the eye surface. Following eye drop administration the peak concentration of agents in the anterior chamber is commonly reached after 20-30 min, and is typically two orders of magnitude lower than that applied. From the aqueous humor the agent has an easy access to the iris, ciliary body, lens and retina. Some part of topically administered drugs may absorb across the bulbar conjunctiva to the sclera and further to the uvea and posterior segment. The passage of agents through the cornea is a non-invasive method for allowing drugs to pass into the posterior segment. The corneal route of delivery is useful not only for therapies but also diagnostic methodologies.

It is of particular interest to be able to deliver cell death markers to the posterior region of the eye and especially to the retina in order to monitor cell death associated with degenerative diseases such as glaucoma. Previously, it has been necessary to deliver cell death markers, such as annexins, intra-vitreously or intra-venously.

The inventors have surprisingly found that Vitamin E derivatives, especially tocopherols may be used as carriers, to enhance the delivery of agents such as annexins to the posterior region of the eye following topical application.

According to the invention there is provided a pharmaceutical composition comprising a Vitamin E derivative and a cell death marker.

Also provided is the use of a Vitamin E derivative as a carrier to deliver an agent to the posterior segment of the eye.

Further provided is a method of delivery of an agent to the posterior region of the eye, comprising administering the agent topically to the eye, in combination with a Vitamin E derivative.

The term Vitamin E derivative is used herein to refer to a tocol or tocotrienol derivative with similar biological activity to α-tocopherol. In particular, the term refers to tocopherols and tocotrienols. There are 8 Vitamin E isomeric molecules: the four tocopherols possess a 4',8',12'-trimethyltridecyl phytol side chain and the four tocotrienols differ by the presence of double bonds at the 3',7' and 11' positions of the side chain. The term also encompasses molecules that are derivatives of tocopherols and tocotrienols, or which are variants of those molecules, having slightly different structures but which have similar functionality.

Vitamin E is comprised of two homologous series of tocochromanols, termed "tocopherols" and "tocotrienols." In particular, a tocopherol is a mono, di or tri-methyltocol, which may have vitamin E activity. The term is well known in the art. Also included in the definition of tocopherol intended herein are derivatives of tocopherol, particularly functional derivatives, that is to say those that retain the carrier function of the parent molecule. An example of a tocopherol derivative is TPGS (D-α-tocopherylsuccinate esterified to polyethyleneglycol 1000). A tocotrienol is a tocol with three double bonds in the side chain, i.e., with three additional double bonds in the phytyl chain, thus a 6-(3',7',11',15'-tetramethyl-2',6',10',14'-hexadecatetraenyl)-1,4-hydroquinone or a 2-methyl-2-(4,8,12-trimethyltrideca-3,7,11-trienyl) chroman-6-ol. The natural products carry methyls at one or more of positions 5, 7, and 8 of the chromanol and are thus identical, except for the unsaturation in the phytyl-like side chain, to the tocopherols; also analogous is the cyclization to form a chromanol derivative and oxidation to form the tocotrienolquinones (or chromenols). Tocotrienol terminology is used to indicate relationships to tocols and tocoenols (vitamin E-like), the chromanol terminology to indicate relationship to the isoprenoidal compounds of the vitamin K and coenzyme Q series.

The term 'cell death marker' refers to a marker that allows live cells to be distinguished from cells that are dying or have died. For example it may be a compound or molecule that specifically binds to live cells but not to dead or dying cells, or that specifically binds to dead or dying cells but not to live cells. Cell death markers include, for example the annexin family of proteins. Annexins are proteins that bind reversibly to cellular membranes in the presence of cations. Annexins useful in the invention may be natural or may be recombinant. The protein may be whole or maybe a functional fragment, that is to say a fragment or region of an annexin that binds specifically to the same molecules as the whole protein. Also included are functional derivatives of such proteins. In particular, the term is considered to encompass molecules containing an "annexin repeat", that is a domain of approximately 70 amino-acids that is conserved both within individual annexins and also between members of the family. A variety of annexins are available, such as those described in US Patent Application Publication No. 2006/0134001A. A preferred annexin is annexin V, which is well known in the art. Other annexins include 2, 6 and 11. Other markers of cell death, especially apoptosis are known in the art, including for example the C2A domain of synaptotagmin (Jung et al., Bioconjing Chem. 2004 September-October; 15(5): 983-7) and propidium iodide.

The cell death marker may be labelled with a fluorescent or other visible or identifiable label. For example, the cell death marker may be labelled with an infrared or near infrared label, in particular an infrared dye. The cell death marker may be labelled using standard techniques.

The term posterior segment of the eye refers to structures at the rear of the eye including, for example the lens, trabecular meshwork, uvea (including the ciliary body), vitreous and retina. In particular, the invention allows improved delivery to the retina.

Tocopherols may also be used in the administration of other active agents and pharmaceuticals, such as neuroprotectants (such as Memantine), growth factors and growth factor-antagonists (including anti-angiogenic molecules), antibodies (such as Lucentis and Avastin), aptamers (such as Macugen), steroids (such as Triamcinolone), molecular agents. The international non-proprietary equivalents of the trademarks Lucentis and Avastin are ranibizumab and bevacizumab, respectively.

The composition of the invention may also include at least one of phosphatidylserine (or similar molecule such as phosphatidylethanolamine) and cholesterol or derivative thereof, such as an oxysterol.

The compositions of the invention may be used to deliver other molecules, agents or compositions to the posterior region of the eye. Accordingly, the composition may additionally contain one or more agents to be delivered. Such agents may include therapeutically or biologically active agents, for example.

A pharmaceutical composition of the invention is formulated to be compatible with its intended route of administration. Methods to accomplish the administration are known to those of ordinary skill in the art. For example, the administration may be intravenous, intraperitoneal, intramuscular, intravitreous, intracavity, subcutaneous or topical.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases. Such preparations may be enclosed in ampoules, disposable syringes, or multiple dose vials.

Solutions or suspensions used for intravenous or intravitreous administration may include a carrier such as physiological saline, bacteriostatic water, CremophorELT"" (BASF, Parsippany, N.J.), ethanol, or polyol. The non-proprietary equivalent of the trademark CremophorELT is polyethoxylated castor oil. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (mannitol and sorbitol), or sodium chloride may be included in the composition. Prolonged absorption of the composition can be accomplished by adding an agent which delays absorption, e.g., aluminium monostearate and gelatin.

The pharmaceutical composition according to the invention is preferably for topical administration, that is to say, preferably for application to the surface of the eyeball, in the form of eye drops or other topical form. Accordingly, the pharmaceutical composition may additionally contain other carriers, vehicles or excipients such as sodium chloride, benzalkonium chloride, sodium dihydrogen phosphate monohydrate, anhydrous disodium phosphate, and water for injections.

Also provided is the use of a Vitamin E derivative as a carrier for the delivery of at least one agent to the posterior region of the eye. The Vitamin E derivative may be used in conjunction with a cell death marker, for example pharmaceutical compositions as discussed above may be used as the carrier. The carrier may be used to deliver therapeutic, diagnostic or other agents to retina and surrounding areas. Methods for delivering such agents are also provided.

BRIEF DESCRIPTION OF THE DRAWINGS

The invention will now be described in detail by way of example only, with reference to the figures in which.

EXAMPLES

Figure 1:
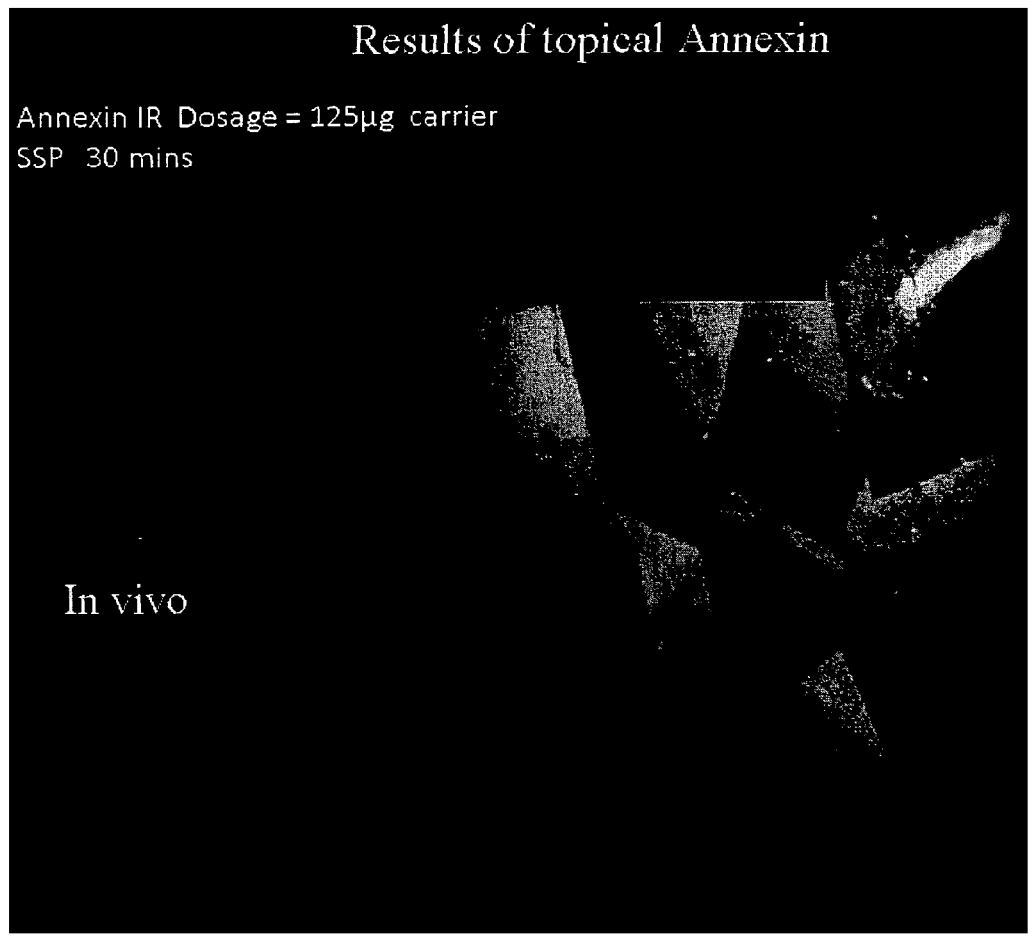
FIG. 1 is a DARC image of a rat retina taken 30 minutes after treatment with topical annexin V after induction of apoptosis by treatment with intravitreal staurosporine (SSP). The image shows clearly that the infrared annexin V can be detected in the retina, labelling the retinal ganglion cell apoptosis induced by SSP.
Figure 2A:
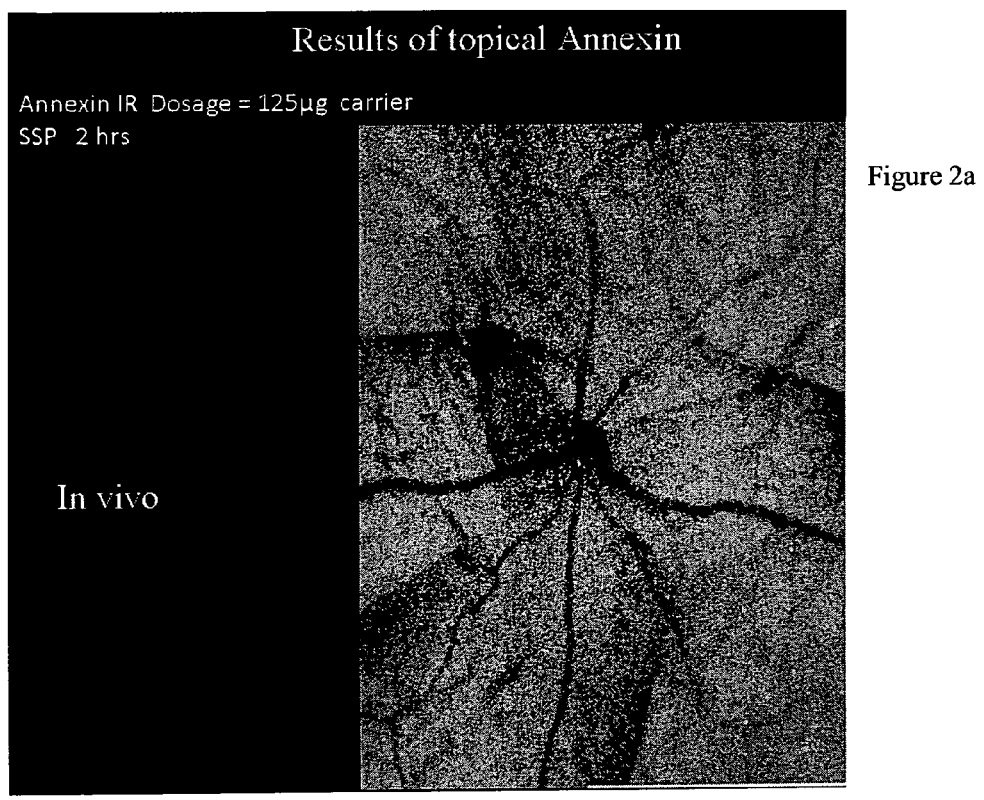
FIG. 2a is a DARC image of a rat retina taken 2 hours after treatment with topical annexin V after induction of apoptosis by treatment with intravitreal staurosporine (SSP). The image shows clearly that the infrared annexin V can be detected in the retina, labelling the retinal ganglion cell apoptosis induced by SSP.
Figure 2B:
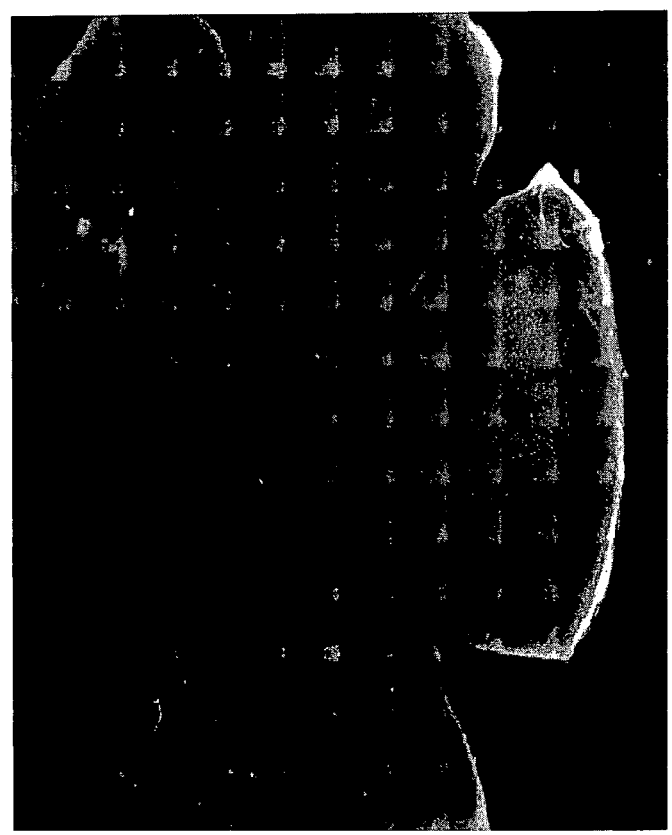
FIG. 2b is the associated histological image.

FIGS. 1 and 2 demonstrate that tocopherol can be used to deliver Annexin V to the eye.

Fluorescently labelled annexin V mixed with tocopherol was administered topically to the eye two hours after treatment with intravitreal staurosporine (SSP) to induce apoptosis. Cell death in the eye was measured using DARC imaging.

Example 1

Delivery of Infrared-Labelled Annexin V to the Eye for DARC (Detection of Apoptosing Retinal Cells) Imaging Stautosporine (SSP) was administered intra-vitreally to a rat eye to induce apoptosis of retinal ganglion cells (RGC). Two hours later infrared labelled annexin V mixed with tocopherol was given topically. The eye was imaged using the DARC (Detection of Apoptosing Retinal Cells) technique[1] with a modified cSLO (confocal scanning laser opthalmoscope) at 790 nm (Heidelberg Retina Angiograph 2, Heidelberg Engineering, Dossenheim, Germany)[1, 2, 3]. The standard lens (15°×15° to 30°×30°) and the wide-field lens (55°—all degree values calibrated for the human eye) were used. Reflectance and corresponding fluorescent images with different focus settings were taken of the rat retina. To improve the signal-to-noise ratio and to enhance image contrast, the mean image output of a series of single images (up to 100) was calculated after correction of eye movements.

Infrared annexin V can clearly be seen in the retina, showing apoptosing cells. FIG. 2 was generated by taking a further image two hours later.

Example 2

Different Vitamin E Derivatives Used for Carrier

Vitamin E is used as the generic description for all tocol and tocotrienol derivatives, with similar biological activity as α-tocopherol—the first characterized molecule (1). There are 8 Vitamin E isomeric molecules: the four tocopherols possess a 4',8',12'-trimethyltridecyl phytol side chain and the four tocotrienols differ by the presence of double bonds at the 3',7' and 11' positions of the side chain.

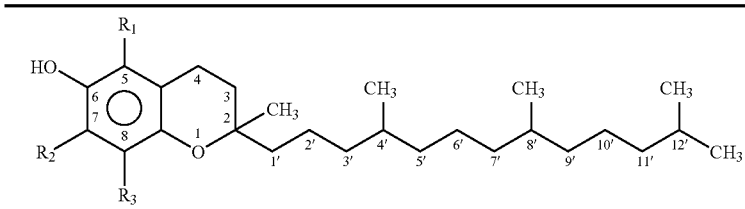

(a). Tocol

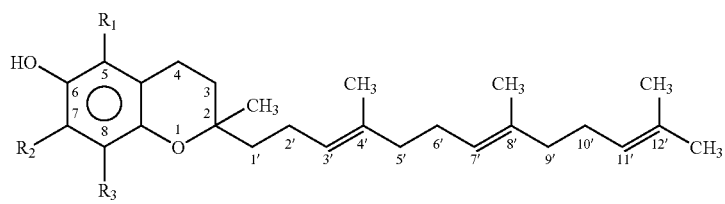

(b). Tocotrienol

| Tocopherol/Tocotrienol | $R_1$ | $R_2$ | $R_3$ |
|---|---|---|---|
| α- | $CH_3$ | $CH_3$ | $CH_3$ |
| β- | $CH_3$ | H | $CH_3$ |
| γ- | H | $CH_3$ | $CH_3$ |
| δ- | H | H | $CH_3$ |

The inventors have assessed all the above, and the images in FIG. 3 show examples of a combination of fluorescent-labelled Annexin 5 (Anx-F) with different Vitamin E derivatives as carriers 1 hour after topical administration. Note the white spots (annexin 5 positive labelling of cells) in the images confirm the passage of the combination through the cornea, vitreous and onto the retina.

Figure 3A:
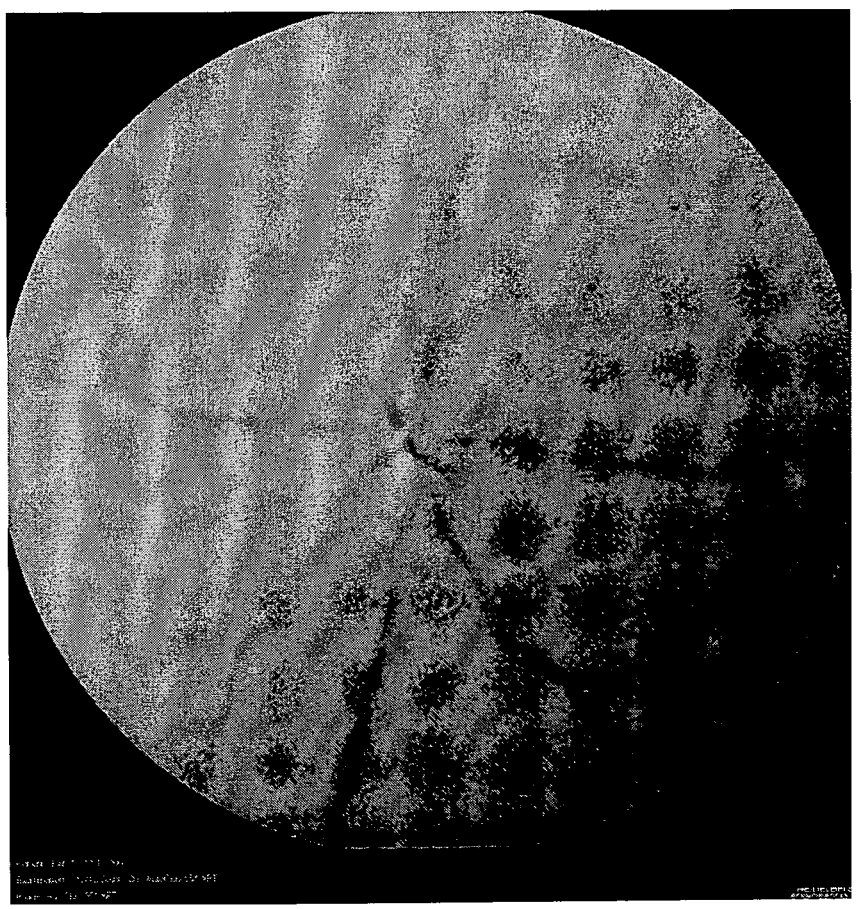
FIG. 3 shows examples of a combination of fluorescent-labelled Annexin 5 (Anx-F) with different Vitamin E derivatives as carriers 1 hour after topical administration.
Figure 3B:
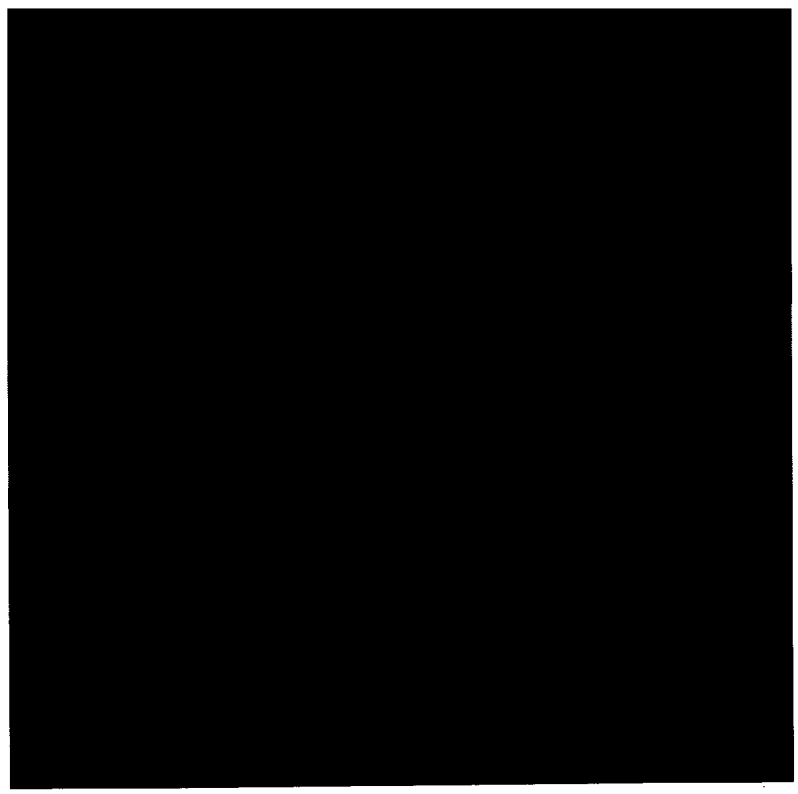
Figure 3C:
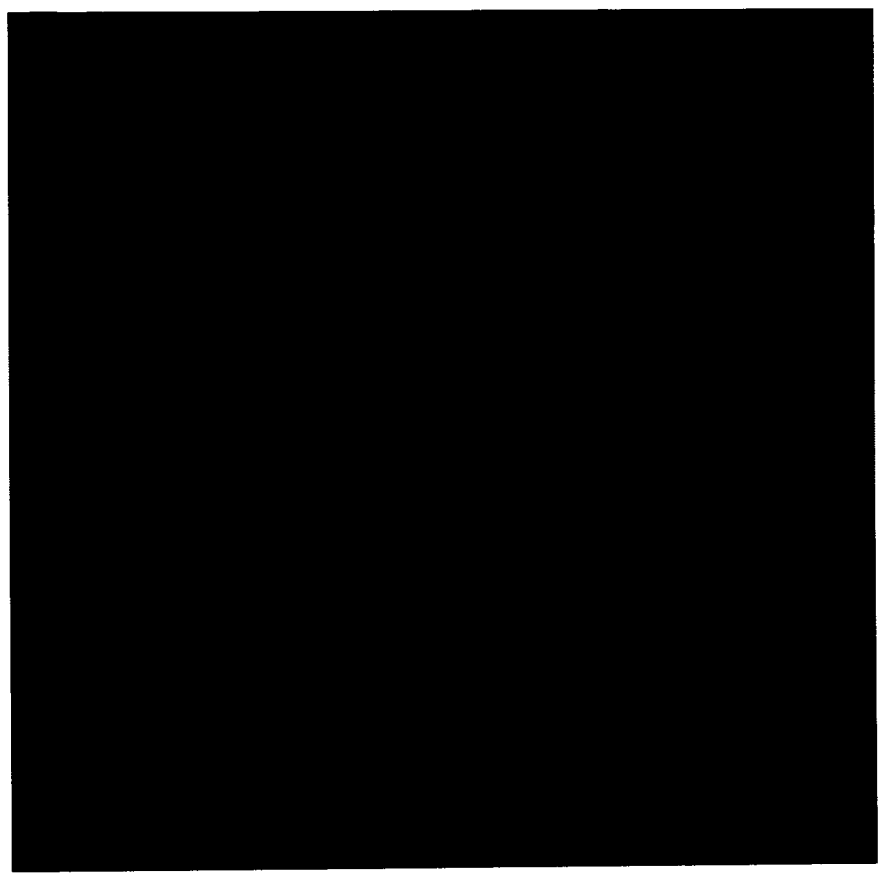
Figure 3D:
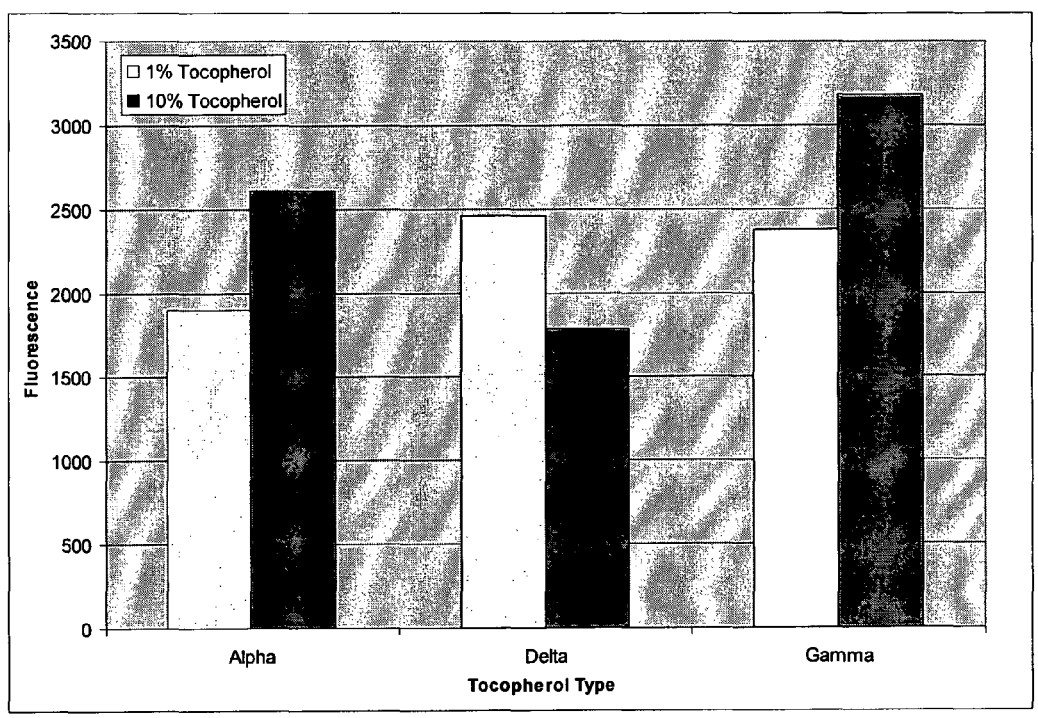

The graph in FIG. 3*d* shows the activity of each of the tocopherols as shown by the fluorescence corresponding to levels of annexin. PC:PS:Chol:Toc membranes containing either 1 or 10% Tocopherol.

Figure 4:
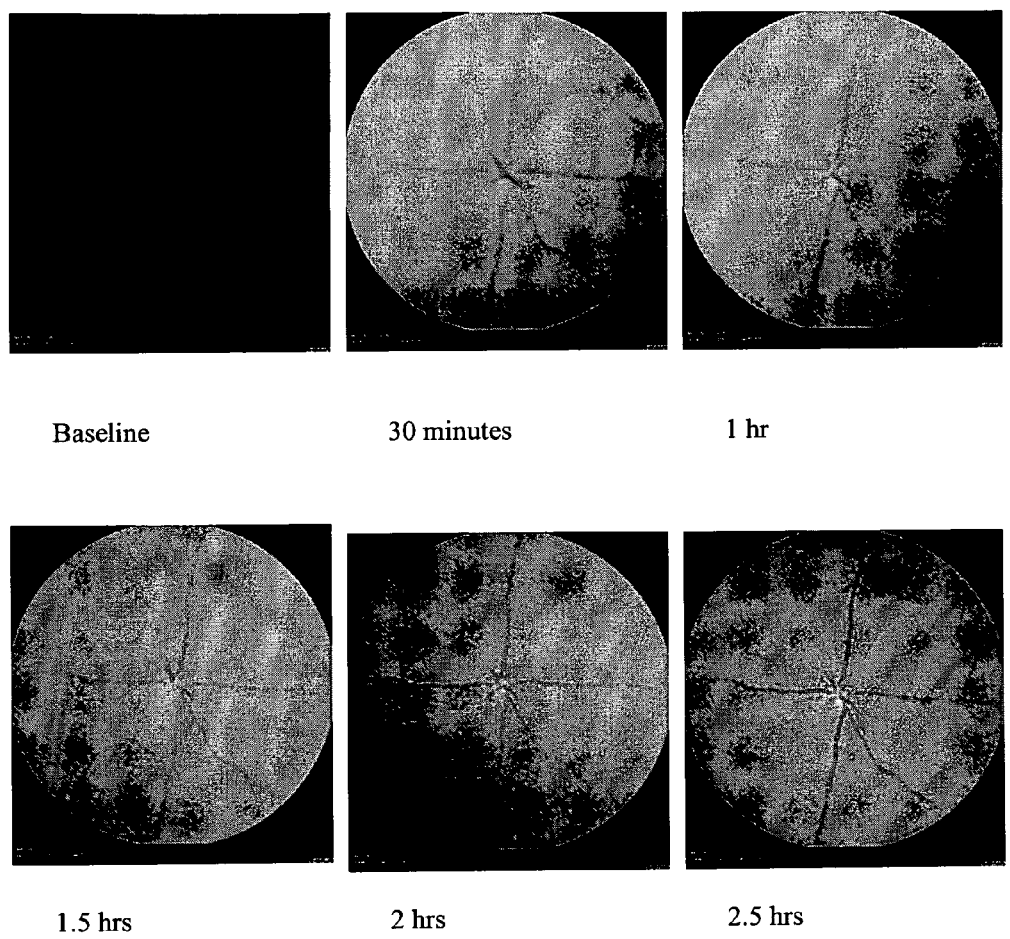
FIG. 4 contains images of the eye showing a time sequence of passage, using α-tocopherol Anx-F applied to the eye, the images were taken at indicated time points after topical administration.

The inventors have also established a time sequence of passage, as shown in FIG. 4, using α-tocopherol Anx-F applied to the eye with images taken at indicated time points after topical administration.

The inventors believe that the reason for the clarity of the image at 2.5 hours is because at this point the fluorescence in the vitreous has cleared or settled. Importantly however, activity in the retina is apparent as early as 30 minutes after topical administration.

Example 3

Different Annexins Used for Carrier

Figure 5:
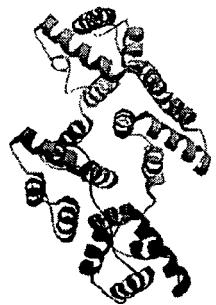
FIG. 5 shows the crystal structure of Annexin 5 (shown left), which is a prototype for all members of the annexin family. The highly alpha-helical core of the protein contains the calcium-binding sites, and is conserved in annexins throughout evolution.
Figure 6:
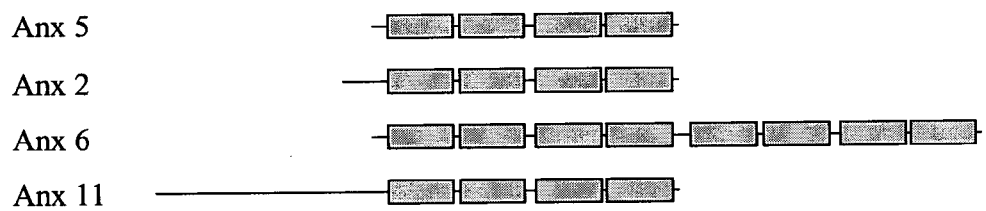
FIG. 6 shows linear schematic representations of Annexins 5, 2, 6 and 11. The N-termini are to the left and the C-termini to the right. The core of each protein is represented by the shaded grey boxes, each one of which corresponds to the well known 'annexin repeat', a domain of approximately 70 amino-acids that is conserved both within individual annexins and also between members of the family.

Since the combination of tocopherol/tocotrienol with Annexin 5 mediates trans-scleral delivery of the annexin to the retina, the question arises as to whether this effect is specific to Annexin 5 or a generic annexin property. The inventors tested this using other annexins such as Annexins 2, 6 and 11, and found that all may be used in the carrier composition (see later). The structure of Annexin 5 is shown in FIG. 5 (taken from Huber, R., Berendes, R., Burger, A., Schneider, M., Karshikov, A., Luecke, H. Romisch, J., Paques, E. (1992). Crystal and molecular structure of human annexin V after refinement. Implications for structure, membrane binding and ion channel formation of the annexin family of proteins. J. Mol. Biol. 223:683-704) in three dimensions, and below in two dimensions along with those of annexins 2, 6 and 11 (FIG. 6).

These annexins differ from Annexin 5 by having a slightly longer N-terminus, a duplication of the tetrad repeat, and a much longer N-terminus respectively. Since all Annexins tested may be used in the carrier composition, we attribute this generic property to the conserved annexin repeat', this being the only molecular determinant common to all four proteins.

Figure 7:
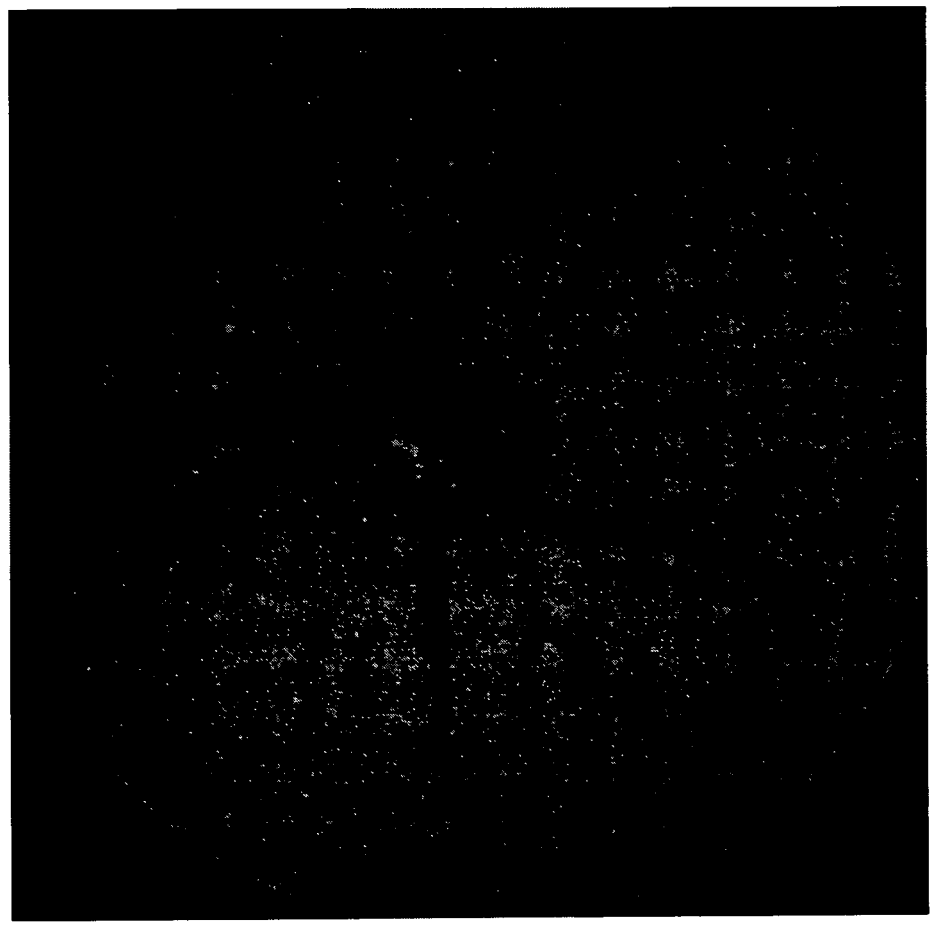
FIG. 7 shows an in vivo image obtained using fluorescent-labelled Annexin 11 with α-tocopherol of the same eye at 2 hours after topical administration.

The in vivo image in FIG. 7 was obtained using fluorescent-labelled Annexin 11 with α-tocopherol of the same eye at 2 hours after topical administration. The white spots clearly demonstrate that Annexin 11 may be used in the carrier composition to detect apoptosis in vivo.

Example 4

Combination of Annexins with Vitamin E Constitutes Optimized Carrier

Figure 8:
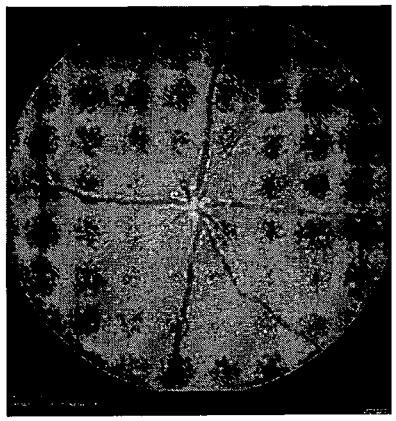
FIG. 8 shows the results of an assay testing the combination of a vitamin E derivative and a cell death marker.
Figure 8:
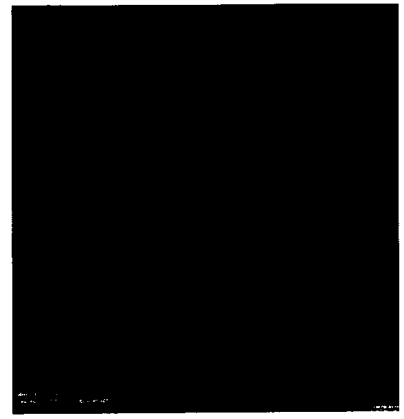
Figure 8:
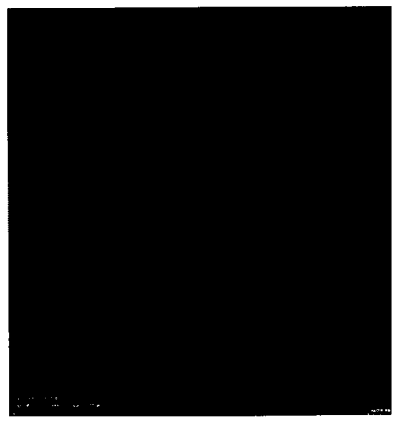
Figure 8:
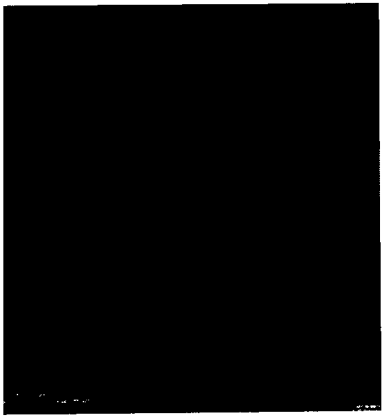
Figure 8:
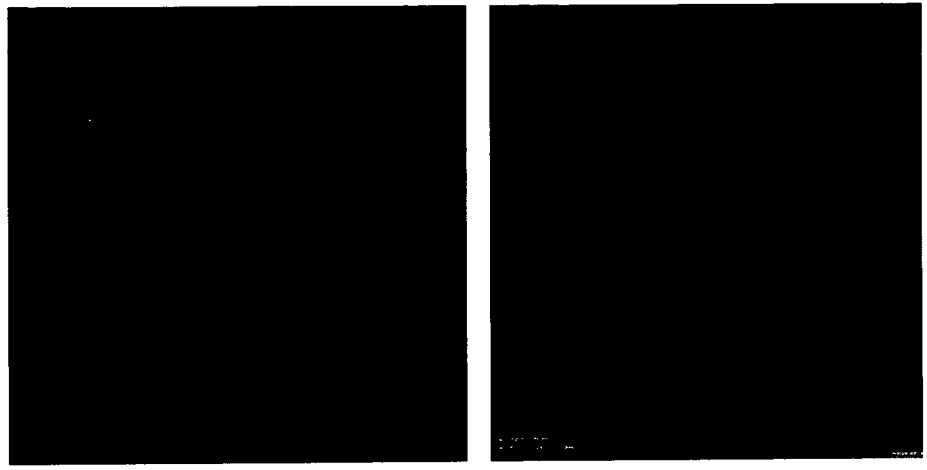
Figure 8:
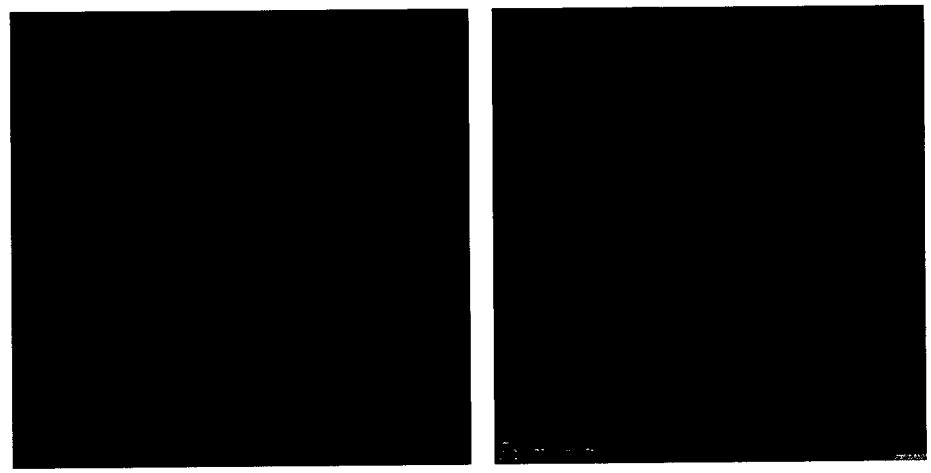

The inventors have shown that it is only the combination of Annexins with the Vitamin E molecules/derivatives that is transported across the cornea following application as an eyedrop into the eye. For example, neither annexin 5 nor annexin 11 enter the eye by themselves when delivered topically. Also, as further examples, neither α-tocopherol with ovalbumin, nor α-tocopherol with dextran enters the eye. Likewise δ-tocopherol and γ-tocopherol do not enter the eye unless administered as a complex with annexin, as can be seen in FIG. 8.

Our findings also suggest that the combination of annexin with Vitamin E derivatives may be augmented and/or regulated by phosphatidylserine and cholesterol. Altering the concentrations of each of these 4 molecules greatly affects the efficacy of trans-scleral and transcorneal delivery.

Example 5

Delivery of Cargo to the Posterior of the Eye

Figure 9:
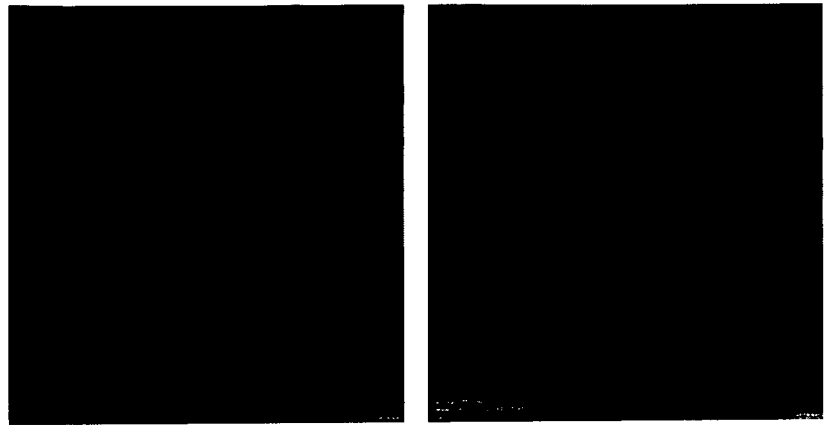
FIG. 9 shows the results of an assay testing the delivery of cargo to the posterior segment.
Figure 9:
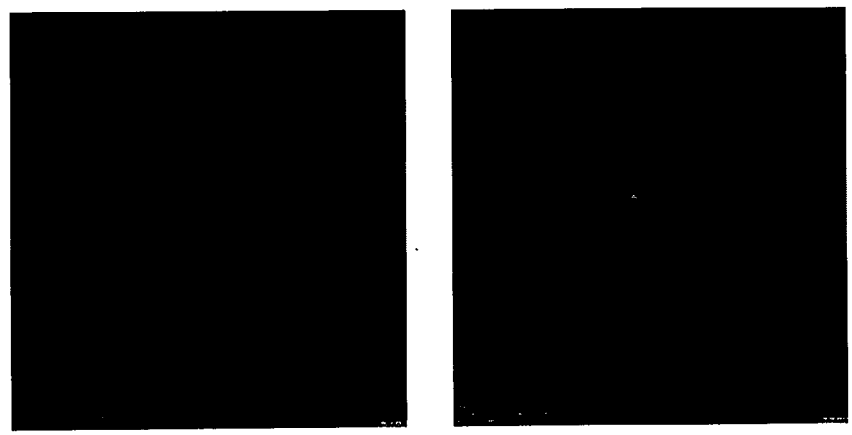

As shown in FIG. 9, it is possible to use the compositions of the invention to deliver other agents or cargo to the posterior region of the eye. Both examples illustrate an increase in the level of background fluorescence after administration, confirming the passage of the cargo to the back of the eye.

Example 6

Delivery to Other Parts of the Eye

Our studies so far have demonstrated that when an Annexin is given topically in combination with a Vitamin E derivative, the fluorescently tagged Annexin (or other fluorescent molecule) can be detected in the retina.

For the carrier Anx-F to reach the retina from the outside of the eye, it has to pass through the cornea, enter the aqueous humour of the anterior and posterior chambers (where it comes into contact with, the iris, ciliary body, trabecular meshwork (TM) and lens) and then back into the vitreous, from where it passes to the retina.

Figure 10:
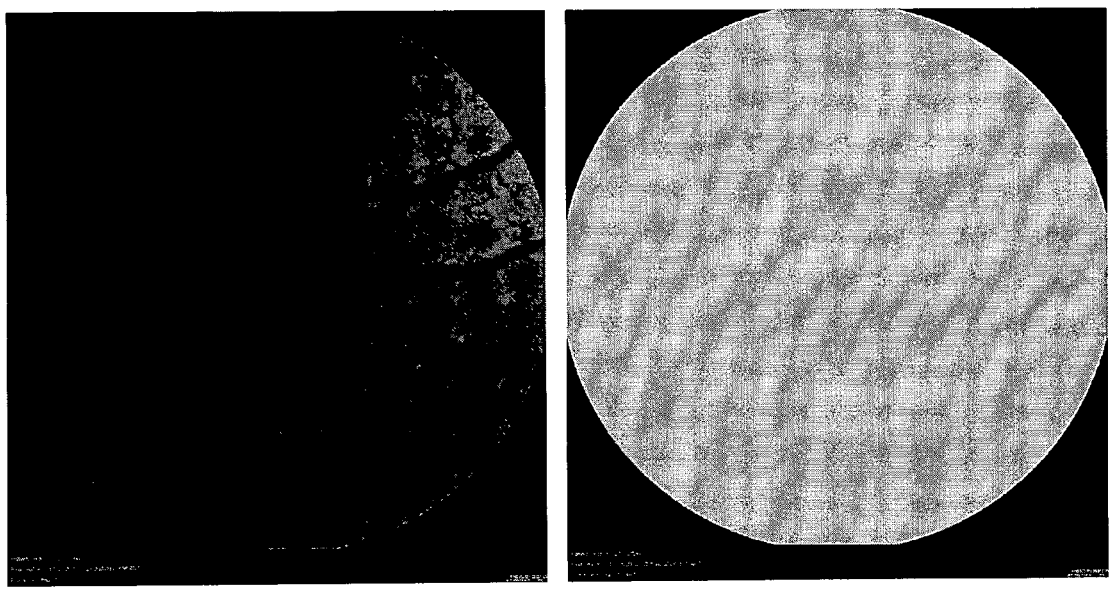
FIG. 10 shows fluorescent-labelled Annexin with α-tocopherol in the same eye at baseline (left) and 1 hour after administration (right), with focussing in the plane in front of the retina.

The in vivo images in FIG. 10 show fluorescent-labelled Annexin with α-tocopherol in the same eye at baseline (left) and 1 hour after administration (right), with focussing in the plane in front of the retina. The bright fluorescent signal is obtained due to fluorescence in the vitreous.

The carrier in combination with an appropriate diagnostic or therapeutic cargo can therefore be used to target any of the tissues shown above, and is thus applicable to diseases such as glaucoma, cataract, uveitis, diabetic retinopathy (DR), retinal detachment (RD) and AMD (age-related macular degeneration). We believe our carrier combination will be applied to treatments such as for AMD & DR, where currently anti-VEGF therapies are administered as an intravitreal injection.

REFERENCES

1. Cordeiro M F, Guo L, Luong V, et al. Real-time imaging of single nerve cell apoptosis in retinal neurodegeneration. *Proc Natl Acad Sci USA* 2004; 101: 13352-13356.
2. Guo L, Salt T E, Luong V, et al. Targeting amyloid-{beta} in glaucoma treatment. *Proc Natl Acad Sci USA* 2007.
3. Maass A, Lundt von Leithner P, Luong V, et al. Assessment of rat and mouse RGC apoptosis imaging in-vivo with different scanning laser opthalmoscopes. *Curr Eye Res* 2007; [accepted for publication].

The invention claimed is:

1. A pharmaceutical composition, comprising: a combination of a Vitamin E derivative and a cell death marker, wherein the cell death marker is annexin V or a functional fragment or derivative thereof that binds reversibly to cellular membranes in the presence of cations.

2. The pharmaceutical composition of claim 1, wherein the Vitamin E derivative is a tocopherol or a derivative thereof.

3. The pharmaceutical composition of claim 2, wherein the tocopherol is D-[alpha]-tocopherylsuccinate esterified to polyethyleneglycol 1000.

4. A method of delivering a cell death marker to a posterior segment of an eye, comprising: administering the pharmaceutical composition of claim 1 to the eye.

5. The method of claim 4, wherein the Vitamin E derivative is D-[alpha]-tocopherylsuccinate esterified to polyethyleneglycol 1000.

6. The method of claim 4, wherein the pharmaceutical composition is formulated for topical delivery.

7. The method of claim 4, wherein the biologically or therapeutically active agent and pharmaceutical composition are delivered topically.

8. The method of claim 7, wherein the Vitamin E derivative is D-[alpha]-tocopherylsuccinate esterified to polyethyleneglycol 1000.

9. The method of claim 4 further comprising delivering a neuroprotectant, a growth factor, a growth factor antagonist, an antibody, an aptamer, or a steroid to the eye.

10. The pharmaceutical composition of claim 1, wherein the composition further comprises one or more additional components selected from physiological saline, bacteriostatic water, polyethoxylated castor oil, ethanol and polyol.

11. A pharmaceutical composition comprising a Vitamin E derivative; and a cell death marker, wherein the cell death marker is an annexin or functional fragment or derivative thereof that binds reversibly to cellular membranes in the presence of cations and wherein the Vitamin E derivative is D-[alpha]-tocopherylsuccinate esterified to polyethyleneglycol 1000.

12. The pharmaceutical composition of claim 11, wherein the annexin is annexin V.

13. The pharmaceutical composition of claim 11, wherein the composition further comprises one or more additional components selected from the physiological saline, bacteriostatic water, polyethoxylated castor oil, ethanol and polyol.

14. The pharmaceutical composition of claim 1, wherein the composition further comprises phosphatidylserine and/or phosphatidylethanolamine.

15. The method of claim 9 wherein the neuroprotectant is memantine or the antibody is selected from ranibizumab and bevacizumab.

* * * * *